United States Patent [19]

Tabara

[11] Patent Number: 4,493,897
[45] Date of Patent: Jan. 15, 1985

[54] METHOD FOR MEASURING AN ELECTROLYTE IN AN AUTOMATIC BIOCHEMICAL ANALYZING APPARATUS WHEREIN A FLAME PHOTOMETER IS ASSEMBLED

[75] Inventor: Takashi Tabara, Hachioji, Japan

[73] Assignee: Olympus Optical Company Limited, Tokyo, Japan

[21] Appl. No.: 281,217

[22] Filed: Jul. 7, 1981

[30] Foreign Application Priority Data

Jul. 9, 1980 [JP] Japan ................................ 55-93570
Jul. 9, 1980 [JP] Japan ................................ 55-93571

[51] Int. Cl.³ .................... G01N 35/02; G01J 3/30; G01N 21/72
[52] U.S. Cl. .................... 436/47; 356/315; 356/417; 422/63; 422/64; 422/65; 436/43; 436/74; 436/79; 436/171
[58] Field of Search .............. 356/315, 417; 422/63–67; 436/43, 47, 74, 79, 171

[56] References Cited

U.S. PATENT DOCUMENTS

| | | | |
|---|---|---|---|
| 2,554,414 | 5/1951 | McClendon | 422/91 |
| 3,526,480 | 9/1970 | Findl et al. | 422/66 |
| 3,586,446 | 6/1971 | Findl et al. | 356/417 |
| 4,054,415 | 10/1977 | Seligson et al. | 422/64 |
| 4,325,910 | 4/1982 | Jordan | 356/434 |

*Primary Examiner*—Michael S. Marcus
*Attorney, Agent, or Firm*—Parkhurst & Oliff

[57] ABSTRACT

An electrolyte in a sample is stably measured by using an automatic biochemical analyzing apparatus wherein a flame photometer is assembled, which comprises a sample pipetting and delivering member, a reagent liquid delivering member, reaction cups charging the sample delivered through the sample pipetting and delivering member and the reagent liquid delivered through the reagent delivering member and a flame photometer for measuring an electrolyte, the method being characterized in that with respect to a sample cup to which the measurement of electrolyte is ordered, the sample pipetting and delivering member and the reagent delivering member are operated to deliver the sample and the reagent liquid to a reaction cup and an electrolyte of the diluted sample in the reaction cup is measured by the flame photometer and with respect to a sample cup to which the measurement of electrolyte is not ordered, the sample pipetting and delivering member is not operated and into a reaction cup corresponding to said sample cup is delivered a liquid from a liquid delivering member and this liquid is fed into a flame photometer and automatically measured to prevent the elevation of the temperature at the flame photometer. The liquid delivered into the reaction cup may be the said reagent liquid or a liquid different from the said reagent liquid. The calibration of the measurement is made in a specific embodiment for carrying out the above mentioned method.

3 Claims, 2 Drawing Figures

FIG_1
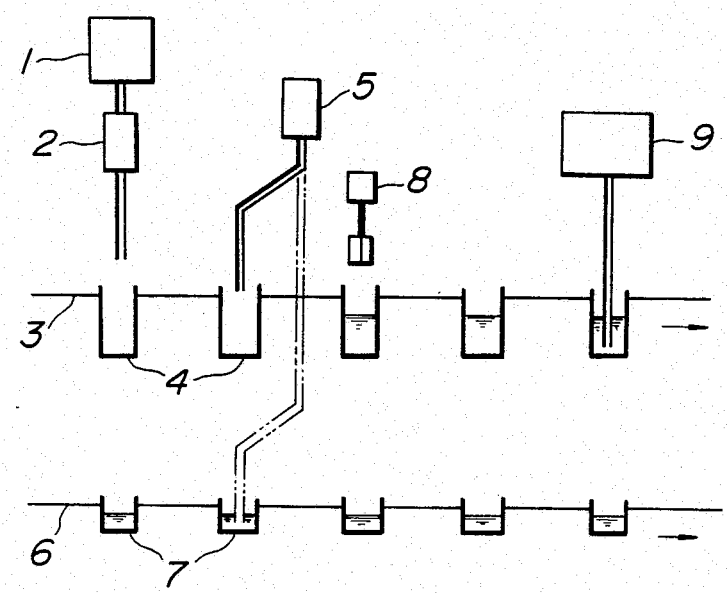
FIG_2
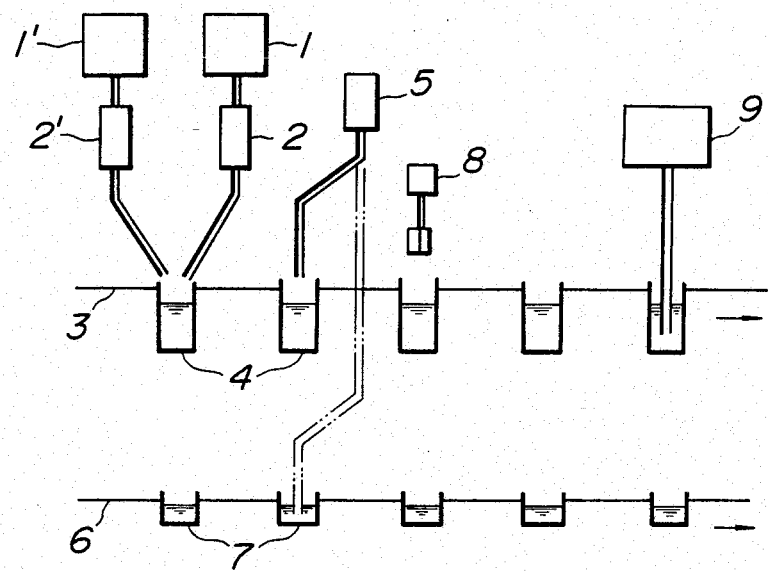

METHOD FOR MEASURING AN ELECTROLYTE IN AN AUTOMATIC BIOCHEMICAL ANALYZING APPARATUS WHEREIN A FLAME PHOTOMETER IS ASSEMBLED

The present invention relates to an automatic biochemical analyzing apparatus wherein a flame photometer is assembled, and particularly to a method for measuring an electrolyte in an automatic biochemical analyzing apparatus which can select a sample to be tested.

Heretofore, in measurement of an electrolyte by using a flame photometer, it has never been necessary to take selecting of a sample into consideration in any case of a manual apparatus or an automatic apparatus. This is because the measurement of electrolytes has been generally carried out by means of an apparatus for attaining a single analyzing objective. However, the improvement and development of automatic biochemical analyzing apparatus have been recently noticeable, and the measurement of electrolytes has been assembled in multi-channels of an automatic analyzing apparatus. When the measurement of electrolytes is combined with the measurement of multi-items and the measurments are concurrently carried out, a sample not needing measurement and a sample needing measurement may be present together and it has been necessary to select the sample to be measured. But in the flame photometer, if a liquid is not injected, for example a temperature in the combustion chamber will be raised and if a liquid is injected, a temperature in the combustion chamber will fall and time is required for stabilizing the flame photometer. Accordingly, when the flame photometer is assembled in the multi-channels of automatic biochemical analyzing apparatus and the electrolyte is measured, in prior analyzing apparatus, if a sample is selected, the data are apt to become unstable and therefore, all samples must be measured even when the measurement is not needed.

An object of the present invention is to provide a method for measuring electrolytes which can obviate the prior defects, maintain the flame photometer in stable condition and select a sample even in an automatic biochemical analyzing apparatus wherein a flame photometer is assembled.

The present invention consists of a method for measuring electrolytes by using an automatic biochemical analyzing apparatus wherein a flame photometer is assembled and which comprises a sample pipetting and delivering member which pipettes a sample liquid and delivers it, a reagent delivering member which removes a reagent liquid to dilute the sample and delivers the reagent liquid, a reaction cup holding the sample delivered from the above described sample pipetting and delivering member and the reagent liquid delivered from the above described reagent delivering member and a flame photometer which measures the electrolyte in the sample diluted with the reagent liquid in the reaction cup, characterized in that with respect to a sample of which measurement of an electrolyte is ordered, the above described sample pipetting and delivering member and the above described reagent delivering member are operated and the sample and the reagent liquid are delivered into a reaction cup from the respective delivering members and an electrolyte in the sample diluted with the reagent liquid in the reaction cup is measured with the above described flame photometer, and with respect to a sample of which the measurement of the electrolyte is not ordered, the above described sample pipetting and delivering member is not operated and a liquid delivered into a reaction cup through the reagent delivering member is fed into the flame photometer and automatically measured.

The present invention is explained in more detail below herein.

For a better understanding of the invention, reference is made to the accompanying drawings, wherein:

FIG. 1 is a flow diagram illustrating operation of an automatic biochemical analyzing apparatus of one embodiment of the present invention; and FIG. 2 is a flow diagram illustrating operation of an automatic biochemical analyzing apparatus of another embodiment of the present invention.

FIG. 1 shows a first example of the present invention. Referring to FIG. 1, numeral 1 denotes a reagent tank and a reagent liquid stored in this tank 1 (for example an internal standard solution of lithium) is delivered into a reaction cup 4 which is transferred in turn to a position on a reaction line 3 where the reagent liquid is delivered by the reagent delivering means 2. Means 5 is a sample pipetting and delivering means for a sample to be measured. The reaction line 3 is transferred in the arrow direction together with a sample line 6 at a given speed. When the reaction cup 4 on the reaction line 3 is transferred to the position where the sample is delivered, a sample to be measured is pipetted from a sample cup 7 on the sample line 6 and delivered into a reaction cup 4 corresponding to a sample cup. The sample pipetting and delivering means 5 is constructed so that it operates when a sample of which the measurement of the electrolyte is ordered, is transferred to the position where the sample is delivered, but does not operate with respect to a sample of which the measurement is not ordered. Then, when the reaction cup 4 on the reaction line 3 reaches a stirring position, a solution in the reaction cup 4 is stirred with a stirrer 8 and then advanced to the measuring position. At the measuring position, the solution in the reaction cup is supplied to the flame photometer 9 and the electrolyte is measured. The transfer of the sample solution into the flame photometer from the reaction cup 4 is effected by the negative pressure of an atomizer in the flame photometer or other means such as a pump.

In this successive operation, with respect to the sample of which the measurement is ordered, the sample diluted with the reagent liquid is supplied to the flame photometer. When a reaction cup 4 corresponding to a sample cup 7 fed with a sample of which the measurement is not ordered is delivered, only the reagent liquid from the reagent delivering means 2 and the reagent liquid is supplied to the flame photometer 9. Accordingly, the reagent liquid is always supplied to the flame photometer, so that a combustion chamber in the flame photometer is maintained at a given temperature without excessively raising the temperature. Therefore, even when the samples of which the measurement is not ordered are continued, if a sample of which the measurement is ordered is subsequently supplied to the flame photometer, the electrolyte in this sample is stably and accurately measured.

FIG. 2 shows a flow diagram illustrating operation of an automatic biochemical analyzing apparatus of a second example according to the present invention. In this example, two reagent tanks 1 and 1' and two reagent delivering means 2 and 2' are provided, different from the first example. In the reagent tank 1', another reagent liquid (for example, lithium concentration: 0–100 mEq/l, sodium concentration: 0–200 mEg/l, potassium concentration: 0–20 mEq/l) different from that of the reagent tank 1 is stored and a reagent delivering means 2' for this reagent liquid is provided. With respect to a reaction cup 4 corresponding to the sample cup 7 wherein the sample of which the measurement is ordered, is charged, the reagent liquid in the tank 1 is delivered by the reagent delivering means 2 into the reaction cup 4 on the reaction line 3, which cup has been transferred to the position where the reagent liquid is delivered. With respect to reaction cup 7 corresponding to the sample cup 7 fed with a sample of which the measurement is not ordered, when this reaction cup is transferred to the position on the reaction line 3 where the reagent liquid is delivered, another reagent liquid in the tank 1' is delivered. Accordingly, the construction is made so that the reagent liquid to be delivered to the reaction cup is selected depending upon the sample of which the measurement is ordered or not. In the first example, the same reagent liquid is delivered irrespective of the order of the measurement, but in order to keep constant the state of the flame photometer, which is the object of the present invention, it is not always necessary to use the same reagent liquid.

In the above described measuring method of the present invention, the reagent liquid is always supplied to the flame photometer irrespective of the sample of which the measurement is ordered, so that the temperature in the combustion chamber in the flame photometer is not excessively high and the temperature can be maintained at a given stable state. Accordingly, even an automatic biochemical analyzing apparatus wherein a flame photometer is assembled, can select the sample of an electrolyte to be measured. Thus, the precision of the automatic biochemical analyzing apparatus can be improved and the sample can be rapidly treated.

When the measurement of an electrolyte in a sample is carried out by means of a flame photometer, the drift of the flame photometer is large and if the temperature in the combustion chamber varies, time is required for stabilizing the temperature, so that calibration (zero adjust, scale check, scale calibration and the like) should be frequently carried out. Accordingly, when a multi-item automatic biochemical analyzing apparatus and a flame photometer are connected, operators have conducted optional and manual calibration or conducted manual calibration at every measurement of respective samples. This is troublesome for the operators and time is required for treatment of multi-samples. Furthermore, when an automatic analyzing apparatus for treating multi-samples is used, the calibration is concurrently applied to analyzing colorimetrically items and an electrolyte, so that the drift cannot be satisfactorily corrected in the measurement of an electrolyte in which the drift is larger than that in the colorimetric analysis.

In the above described example shown in FIG. 2, the calibration of the flame photometer can be automatically carried out.

That is, into a reaction cup 4 on a reaction cup line 3 corresponding to a cup 7 for calibration on a sample cup line 6 is delivered a reagent liquid in a reagent tank 1' by means of a reagent delivering means 2'. This reagent liquid in the reagent tank 1' is a standard sample reagent liquid for calibration prepared by diluting Na and K standard solution which is an electrolyte standard solution having known concentration (for example Na: 145 mEq/l, K: 5 mEq/l) with a reagent liquid (internal standard solution) in a reagent tank 1. The diluting ratio of the reagent liquid is the same as that of serum of a sample. For example, when 20 µl of serum is diluted with 2.0 ml of the reagent liquid in the reagent tank 1, the ratio of serum diluted is 1/101, so that the reagent liquid in the reagent tank 1' is the standard sample reagent liquid prepared by diluting 1 volume of Na-K standard solution with 100 volumes of the reagent liquid in the reagent tank 1. Then the reaction cup wherein the reagent liquid in the reagent tank 1' has been delivered, is transferred to a position where a sample is delivered. However, the sample pipetting and delivering means 5 does not pipet or deliver a sample with respect to a cup for calibration. Accordingly, the reaction cup corresponding to the cup for calibration is transferred to the measuring position in the state where only the standard sample reagent liquid in the reagent tank 1' has been charged and said standard sample reagent liquid is transferred to the flame photometer 9 and the concentration in said reagent liquid is measured. In this case, the concentration in said reagent liquid may be measured as a value different from the original concentration due to the drift of the flame photometer. In this case, a calibrating factor is automatically calculated as follows.

$$\text{Calibrating factor} = \frac{\text{Original concentration of electrolyte standard solution}}{\text{Concentration of the standard sample reagent liquid measured by flame photometer}}$$

A value obtained by measuring a sample with the flame photometer is multiplied by this calibrating factor to obtain a true measured value. For example, the above described concentration of Na and K in Na, K standard solution is 145 mEq/l and 5 mEq/l respectively, but when the concentration of Na and K measured by a flame photometer is 148 mEq/l and 5.4 mEq/l respectively, the calibrating factors of Na and K are $145/148 \cong 0.9797$ and $5.0/5.4 \cong 0.9259$ respectively. In the subsequent measurement of the samples, the values obtained in the measurement using a flame photometer are multiplied by this factor to obtain the true measured values.

With respect to the reaction cups 4 corresponding to the cups 7 on the sample cup line 6 wherein samples to be determined have been charged, the reagent liquid in the reagent tank 1 is delivered by reagent delivering means 2. Then, the reaction cup 4 charged with the reagent liquid in the reagent tank 1 is transferred to a position where a sample is delivered and the sample is delivered into the reaction cup from a cup wherein a sample to be measured is charged, by sample pipetting and delivering means 5 and then the diluted sample is stirred by a stirrer 8. This reaction cup is transferred to the measuring position and for example a diluted serum solution in the reaction cup is transferred to the flame photometer and a concentration of the solution is measured and the measured value is multiplied by the above described calibrating factor to obtain a true concentration.

To a reaction cup 4 corresponding to a sample cup charged with a sample of which the measurement is not ordered, is delivered the standard sample reagent liquid in the reagent tank 1' by reagent delivering means 2'. But even when this reaction cup is transferred to the position where a sample is delivered, the sample pipetting and delivering means 5 does not effect the sampling. Thereafter, the reaction cup is transferred to the measuring position and only the standard sample reagent liquid in the reaction tank 1' is supplied to the flame photometer and measured by the flame photometer. From this measured value, the calibrating factor is calculated as mentioned above and values of the subsequent samples to be determined, measured by the flame photometer, are corrected by using the calibrating factor.

In another example, the calibrating factor calculated from the measured value of the flame photometer as mentioned above is not directly utilized in the subsequent correction but the concentration of the standard sample reagent liquid obtained by measuring it by means of the flame photometer, or the calibrating factor obtained from this measured value, is compared with the value obtained in the preceeding measurement, or the calibrating factor obtained therefrom, and when the different is smaller than a given ratio or a given value, the calibrating factor calculated from the latter measured value is used; however, when said difference is larger, the calibrating factor calculated from the former determined value is used to correct the measured values of the subsequent samples. This is carried out on every sample of which the measurement is not ordered. When a plurality of samples of which the measurement is not ordered, are continued, an average value of the plurality of measured values is compared with the measured value utilized hitherto or to an average value of the measured values and when the difference of both the values is large, the calibrating factor calculated from the average value of the measured values utilized hitherto is thereafter used for the subsequent measurement of the samples and when the difference is small, the calibrating factor obtained from the latter measured value or average value of measured values is used. The biochemical analyzing apparatus wherein items other than the flame photometer are assembled, is constructed so that the calibration of the flame photometer and the calibration of other items can be concurrently effected and the drift between the calibrations is corrected.

According to the present invention, the calibration of the flame photometer is automatically conducted, so that the calibration can be effected in a short time and the time for treating multi-samples can be greatly shortened. Even in the biochemical analyzing apparatus wherein items other than the flame photometer are assembled, calibration between mutual items can be taken into account, so that the drift between calibrations can be corrected and the analyzing precision can be improved. Furthermore, the solution obtained by diluting the standard solution having the already known concentration with the internal standard solution is used for the calibration, so that the variation of measured values due to error and unevenness of sampling for calibration and variation of measured values due to evaporation of serum for calibration can be prevented and the stabilized calibration which is low in the variation within one day or between days can be carried out.

Furthermore, the samples of which the measurement is ordered, are diluted with the reagent liquid and then supplied to the flame photometer and with respect to the samples of which the measurement is not ordered or the cups for calibration, only the standard sample reagent liquid is supplied to the flame photometer, so that there is no case where the temperature in the combustion chamber in the flame photometer is excessively raised and a constant temperature can be maintained. Even when the samples of which the measurement is not ordered, are continued, it is possible to correct the measured values of subsequent samples, so that the measurement of electrolytes can be accurately carried out under a stable state.

Thus, the precision of the automatic biochemical analyzing apparatus wherein the flame photometer is assembled can be improved and rapid treatment of the samples can be carried out.

What is claimed is:

1. A method for measuring an electrolyte concentration in an automatic biochemical analyzing apparatus comprising the steps of:
   (a) providing a series of sample cups, said sample cups each containing a sample;
   (b) ordering a sample pipetting and delivering means to remove a sample from a first sample cup and transfer said sample to a first reaction cup;
   (c) ordering said sample pipetting and delivering means not to remove a sample from a second sample cup and not to transfer said sample from said second sample cup to a second reaction cup;
   (d) ordering a reagent liquid delivering means successively to deliver reagent liquid to each reaction cup in said series of reaction cups;
   (e) successively supplying the contents of each reaction cup to a flame photometer;
   (f) successively analyzing the contents of each reaction cup in said flame photometer;
wherein said reagent liquid delivering means is ordered to deliver a first reagent liquid to said first reaction cup and a second reagent liquid to a second reaction cup, said second reagent liquid comprises a standard sample reagent liquid being prepared by diluting a standard electrolyte solution having a known concentration with said first reagent liquid, said standard sample reagent liquid having a dilution ratio identical to a dilution ratio created when said sample removed from said first sample cup is tranferred to said first reaction cup and diluted with said first reagent liquid, said standard sample reagent liquid being measured by said flame photometer to determine the concentration thereof, a calibrating factor being determined by dividing the concentration of said standard electrolyte solution by the concentration of said standard sample reagent liquid whereby said flame photometer is calibrated by multiplying a measured value of the contents of said first reaction cup by said calibration factor;
   whereby said flame photometer is maintained in a substantially stable operating condition.

2. The method of claim 1, wherein the concentration of said standard sample reagent liquid or said calibrating factor determined therefrom is compared to a concentration value obtained in a preceeding measurement or a calibrating factor determined therefrom, when the difference is less than a predetermined value, the calibrating factor for said standard sample reagent liquid is used instead of said calibrating factor determined for said preceeding measurement.

3. The method of claim 1, wherein a plurality of calibrating factors is determined for said standard sample reagent liquid, and an average value of said plurality of calibrating factors is calculated wherein said average value is used as the calibrating factor.

* * * * *